United States Patent
Ariyoshi

(10) Patent No.: US 9,500,662 B2
(45) Date of Patent: Nov. 22, 2016

(54) SAMPLE ANALYZER AND SAMPLE ANALYZING METHOD

(71) Applicant: Sysmex Corporation, Kobe-shi, Hyogo (JP)

(72) Inventor: Shunsuke Ariyoshi, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 84 days.

(21) Appl. No.: 14/470,353

(22) Filed: Aug. 27, 2014

(65) Prior Publication Data

US 2015/0064795 A1 Mar. 5, 2015

(30) Foreign Application Priority Data

Aug. 30, 2013 (JP) ................................ 2013-179846

(51) Int. Cl.
  *G01N 35/02* (2006.01)
  *G01N 35/00* (2006.01)
(52) U.S. Cl.
  CPC .................. *G01N 35/00693* (2013.01); *G01N 2035/00673* (2013.01); *Y10T 436/11* (2015.01)
(58) Field of Classification Search
  CPC .................................................... G01N 35/02
  USPC ...................... 422/63–67; 436/43–47, 50, 55
  See application file for complete search history.

(56) References Cited

U.S. PATENT DOCUMENTS

| | | | | |
|---|---|---|---|---|
| 4,043,756 A * | 8/1977 | Sommervold | ... | G01N 35/00693 422/64 |
| 5,467,187 A * | 11/1995 | Beers | .................. | G01N 21/534 356/243.2 |
| 5,554,539 A * | 9/1996 | Chadney | .......... | G01N 35/00594 436/8 |
| 5,637,275 A * | 6/1997 | Carey | ..................... | B01L 3/508 366/214 |
| 5,741,708 A * | 4/1998 | Carey | ..................... | B01L 3/508 422/547 |
| 5,807,523 A * | 9/1998 | Watts | ............... | G01N 35/00594 366/168.1 |
| 6,372,503 B1 * | 4/2002 | Samsoondar | .......... | G01N 33/72 436/11 |
| 6,787,361 B1 * | 9/2004 | Klee | ..................... | G01N 33/50 436/43 |
| 7,185,288 B2 * | 2/2007 | McKeever | ......... | G01N 35/0092 422/63 |
| 2003/0194349 A1 * | 10/2003 | Carey | ..................... | B01L 3/508 422/63 |
| 2004/0209375 A1 * | 10/2004 | Diby | ................ | G01N 35/00603 436/50 |
| 2007/0241760 A1 * | 10/2007 | Yamasaki | ............... | G01R 27/28 324/601 |
| 2008/0240988 A1 * | 10/2008 | Wakamiya | ....... | G01N 35/00693 422/68.1 |

FOREIGN PATENT DOCUMENTS

EP  1 975 623 A2  10/2008
JP  60-135842  *  7/1985

(Continued)

Primary Examiner — Arlen Soderquist
(74) Attorney, Agent, or Firm — Brinks Gilson & Lione

(57) ABSTRACT

Disclosed is a sample analyzer comprising: a measurement unit including a reagent storage capable of holding a plurality of kinds of reagents, the measurement unit configured to measure a sample by use of a plurality of kinds of reagents held in the reagent storage in combination; a memory in which a calibration curve is stored in association with a reagent set used in creation of the calibration curve; and a controller programmed to perform operations, comprising: in a case where no calibration curve corresponding to a reagent set used in measurement of the sample has been stored, storing, in the memory, information indicating that the reagent set used in the measurement of the sample has been used in measurement, and when creating a calibration curve, automatically extracting the reagent set for which no calibration curve has been stored and for which the information has been stored.

18 Claims, 16 Drawing Sheets

(56) References Cited

FOREIGN PATENT DOCUMENTS

| | | |
|---|---|---|
| JP | 09-325150 A | 12/1997 |
| JP | 2002-196005 A | 7/2002 |
| JP | 2003-315343 A | 11/2003 |
| JP | 2009-036512 A | 2/2009 |
| JP | 2010-261823 A | 11/2010 |
| JP | 2012-225879 A | 11/2012 |

* cited by examiner

F I G. 1
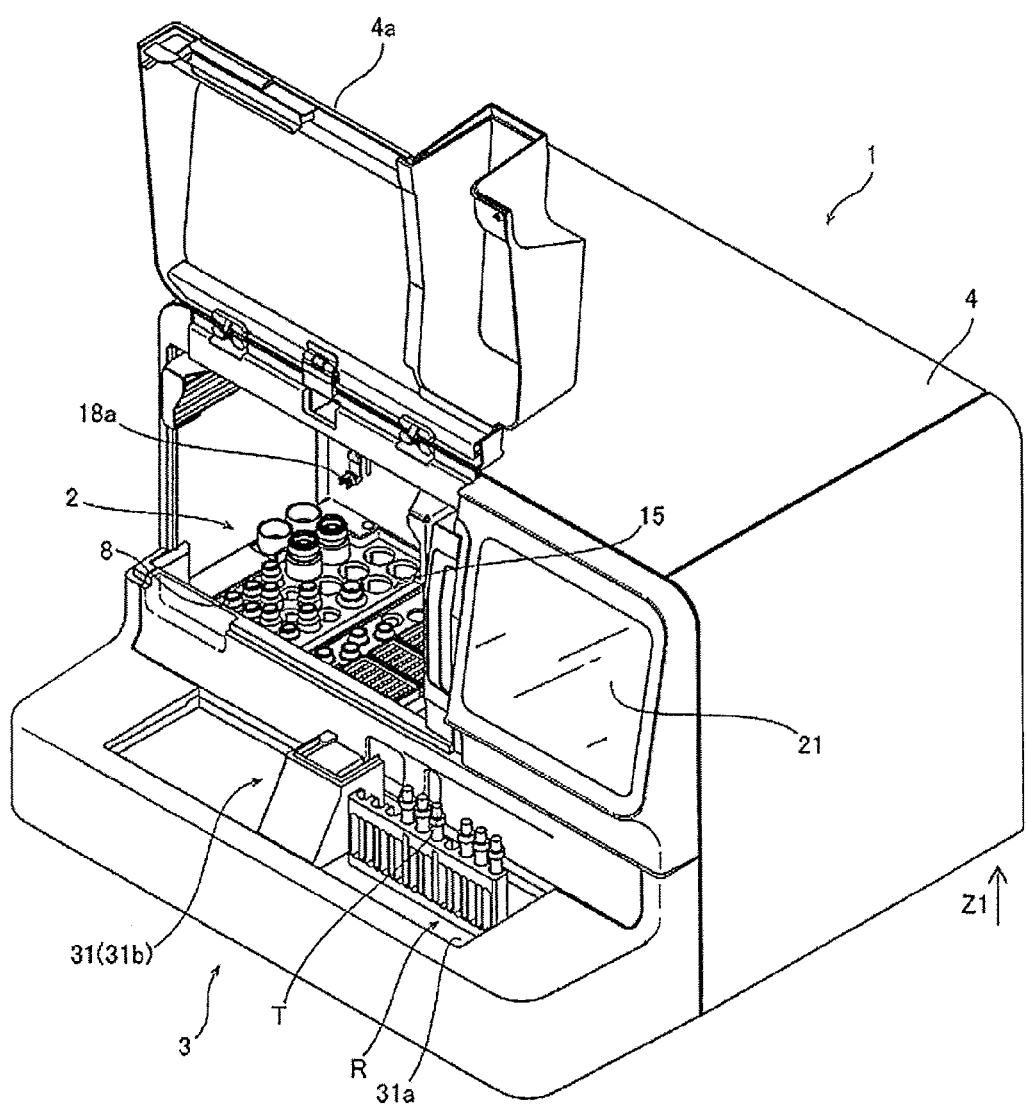

Job List (All Sample-419/419)

Menu  Service  Mainte  Order   [Order ▸]  [Validate]  [Data Operation ▸]  [Browser]  [Display Setting ▸]  [Output ▸]  [Delete]

| ✓ | Measurement State | Sample Number | Rack Number -Position | Date | Start Time | End Time | Output | Seq | Sample Number Input Attribute | Sample Classi-fication | R | Mode |
|---|---|---|---|---|---|---|---|---|---|---|---|---|
| ✓ | Complete | 300071 | 000071-06 | 2012/11/30 | 13:44 | 21:44 | G | 42 | M | | | |
| ✓ | Complete | X-101 | 000072-01 | 2012/11/30 | 13:55 | 21:50 | G | 43 | M | | | M |
| ✓ | Complete | X-102 | 000072-02 | 2012/11/30 | 14:11 | 21:51 | GH | 44 | M | | | M |
| ✓ | Complete | X-003 | 000073-03 | 2012/11/30 | 14:35 | 21:51 | | 45 | M | | | M |
| ✓ | Complete | X-004 | 000073-04 | 2012/11/30 | 14:40 | 21:55 | | 46 | M | | | M |
| ✓ | Complete | X-005 | 000073-05 | 2012/11/30 | 14:49 | 21:59 | | 47 | M | | | M |
| ✓ | Complete | X-006 | 000073-06 | 2012/11/30 | 14:58 | 22:00 | G | 48 | M | | | M |
| ✓ | Complete | 300071 | 000071-06 | 2012/11/30 | 13:44 | 21:44 | | 49 | M | | | |
| | On Hold | 12 | 000074-02 | 2013/04/11 | 20:28 | 20:48 | | 50 | M | | | M |

[Sample Information] [Measurement Result]   [▲▲ ▲ ▼ ▼▼]   STAT   [Measurement Start]  [Suspend Measurement]   Error   End IPU DeviceStatus: 3 Ready
Last ErrorCode: 30310

| Item | | | |
|---|---|---|---|
| Reagent Lot Set | | | |
| AT3Thro/AT3Sub/OVB 536331/520273/– | [Without a Calibration Curve] | ☐ 1 Point Correction | Barcord Info |
| AT3Thro/AT3Sub/OVB 536316/520266/– | [With a New Calibration Curve] [With On Hold] | | ▶ |
| AT3Thro/AT3Sub/OVB 536314/520259/– | [Without a Calibration Curve] | ⏪ ◀ ▶ ⏩ | |
| AT3Thro/AT3Sub/OVB 536312/520257/– | [With a New Calibration Curve] | | |
| AT3Thro/AT3Sub/OVB 536310/520255/– | [With a Validated Calibration Curve] | OK | Cancel |

| Menu | Service | Mainte | Order | | Validate | Data Operation | Browser | Display Setting | Output | | |
|---|---|---|---|---|---|---|---|---|---|---|---|
| | Measurement State | Sample Number | Rack Number -Position | Date | Start Time | End Time | Output | Seq | Sample Number Input Attribute | Sample Classi-fication | R Mode |
| ∨ | Complete | 300071 | 000071-06 | 2012/11/30 | 13:44 | 21:44 | G | 42 | | | |
| ∨ | Complete | X-101 | 000072-01 | 2012/11/30 | 13:55 | 21:50 | G | 43 | M | | M |
| | Complete | X-102 | 000072-02 | 2012/11/30 | 14:11 | 21:51 | | 44 | M | | M |
| ∨ | Complete | X-003 | 000073-03 | 2012/11/30 | 14:35 | 21:51 | GH | 45 | M | | M |
| ∨ | Complete | X-004 | 000073-04 | 2012/11/30 | 14:40 | 21:55 | | 46 | M | | M |
| ∨ | Complete | X-005 | 000073-05 | 2012/11/30 | 14:49 | 21:59 | | 47 | M | | M |
| | Complete | X-006 | 000073-06 | 2012/11/30 | 14:58 | 22:00 | | 48 | M | | M |
| ∨ | Complete | 300071 | 000071-06 | 2012/11/30 | 13:44 | 21:44 | G | 49 | M | | M |
| | Complete | 12 | 000074-02 | 2013/04/11 | 20:28 | 20:48 | | 50 | M | | |

Sample Information | Measurement Result | STAT | Measurement Start | Suspend Measurement DeviceStatus: 3 Ready
Last ErrorCode: 30310

46

F I G. 1 6
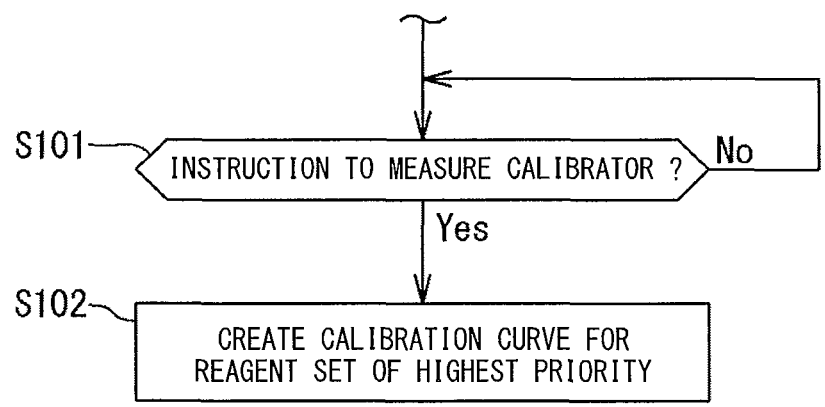

SAMPLE ANALYZER AND SAMPLE ANALYZING METHOD

RELATED APPLICATIONS

This application claims priority under 35 U.S.C. §119 to Japanese Patent Application No. 2013-179846 filed on Aug. 30, 2013, the entire content of which is hereby incorporated by reference.

FIELD OF THE INVENTION

The present invention relates to a sample analyzer which analyzes a sample by use of a plurality of reagents, and relates to a sample analyzing method.

BACKGROUND OF THE INVENTION

Conventionally, there has been known an automatic analyzer which analyzes a sample by use of a reagent, and which has, in order to avoid suspension of measurement due to occurrence of reagent shortage during operation of the analyzer, a function (hereinafter, also referred to as automatic reagent switching) of automatically switching a reagent to be used in measurement to a reagent of the same kind in another reagent bottle, so as to continue measurement (for example, see Japanese Laid-Open Patent Publication No. 2009-36512).

When automatic reagent switching has occurred, the reagent is not always switched to a reagent for which calibration has been performed, and may be switched to a reagent for which calibration has not been performed. In such a case, a target analysis parameter cannot be obtained due to lack of a calibration curve. Thus, after measurement has been performed, it is necessary to execute calibration to create a calibration curve, and then to apply measurement data to the created calibration curve, to recalculate an analysis parameter.

Japanese Laid-Open Patent Publication No. 2002-196005 discloses an analyzer in which: by performing measurement, reaction process of a specimen is detected to be stored, and even in a case of a specimen measured with calibration having failed, calibration is performed again after the measurement, and the data of the stored reaction process is applied to a new calibration curve, thereby allowing recalculation of an analysis parameter to be performed. By utilizing the function as disclosed in Japanese Laid-Open Patent Publication No. 2002-196005, it is possible to create a calibration curve after measurement and to recalculate an analysis parameter.

When an analysis parameter is to be recalculated by performing calibration after measurement of a sample, it is necessary to perform the calibration by use of the reagent that was actually used in the measurement. Thus, when performing calibration, a user needs to designate the reagent used in the measurement. However, in a case of analysis in which a plurality of kinds of reagents are used in combination for measuring one measurement item, a calibration curve needs to be created for each combination of reagent lots, and thus, there exist many combinations of reagent lots serving as targets for creation of a calibration curve, including combinations of unused lots. Conventionally, the user searches, among such many combinations, for a reagent set for which no calibration curve has been created and which includes the reagent lots used in the measurement, and thus, the work is complicated and improvement of convenience has been desired.

SUMMARY OF THE INVENTION

The scope of the present invention is defined solely by the appended claims, and is not affected to any degree by the statements within this summary.

A first aspect of the present invention is a sample analyzer comprising:

a measurement unit including a reagent storage capable of holding a plurality of kinds of reagents, the measurement unit configured to measure a sample by use of a plurality of kinds of reagents held in the reagent storage in combination;

a memory in which a calibration curve is stored in association with a reagent set used in creation of the calibration curve; and a controller programmed to perform operations, comprising:

in a case where no calibration curve corresponding to a reagent set used in measurement of the sample has been stored, storing, in the memory, information indicating that the reagent set used in the measurement of the sample has been used in measurement, and when creating a calibration curve, automatically extracting the reagent set for which no calibration curve has been stored and for which the information has been stored.

A second aspect of the present invention is a sample analyzing method using a sample analyzer, the method comprising:

measuring a sample by use of a reagent set including a reagent for which a calibration curve needs to be created and a plurality of kinds of reagents;

storing the reagent set;

creating a calibration curve by use of the stored reagent set; and determining, by use of the created calibration curve, a component concentration of the sample measured by use of the reagent for which a calibration curve needs to be created.

A third aspect of the present invention is a sample analyzer comprising:

a measurement unit including a reagent storage capable of holding a plurality of kinds of reagents, the measurement unit configured to measure a sample by use of a plurality of kinds of reagents held in the reagent storage in combination;

a memory in which a quality control result is stored in association with a reagent set used in quality control; and a controller programmed to perform operations, comprising:

in a case where no quality control result corresponding to a reagent set used in measurement of the sample has been stored, storing, in the memory, information indicating that the reagent set used in the measurement of the sample has been used in measurement, and when executing quality control, automatically extracting the reagent set for which no quality control result has been stored and for which the information has been stored.

In the present invention, a "reagent set" can be used to mean a combination of reagent lots, or a combination of reagent vials. In the meaning of the former, even when the combination of reagent vials has been changed due to switching of reagents, as long as there is no change in the combination of reagent lots, the reagent set before the switching and the reagent set after the switching are the same. Thus, in this case, a calibration curve created for the reagent set before the switching can be applied also to the reagent set after the switching. On the other hand, in the meaning of the latter, when the combination of reagent vials has been changed due to switching of reagents, even when there is no change in the combination of reagent lots before and after the switching of reagents, the reagent set before the switching, and the reagent set after the switching are considered as different reagent sets. In this case, a calibration curve created for the reagent vial set before the switching of reagents cannot be applied to the reagent vial set after the switching, and thus, it is necessary to newly create a calibration curve for the reagent set including new vials after the switching.

Moreover, in the present invention, "a case where no calibration curve has been stored" includes not only a case where a calibration curve corresponding to a reagent set is not simply stored, but also a case where a valid calibration curve is not stored. The valid calibration curve is a calibration curve which conforms to a rule determined by the analyzer or the user and which can be used in calculation of an analysis parameter. For example, even in a case where a calibration curve corresponding to a reagent set has been stored, if the expiration date of the calibration curve has passed, the calibration curve has not been validated, or the like, such a calibration curve is not valid, and thus, this corresponds to a case where a valid calibration curve is not stored.

BRIEF DESCRIPTION OF THE DRAWINGS

FIG. 1 is a perspective view of one embodiment of a sample analyzer of the present invention;

FIG. 7 shows one example of a reagent management screen;

FIG. 8 shows one example of a sample order registration screen;

FIG. 10 shows one example of a job list screen;

FIG. 11 shows one example of a calibration curve order registration screen;

FIG. 13 shows one example of the calibration curve order input screen;

FIG. 15 shows one example of the job list screen; and

FIG. 16 is a flow chart showing operation performed by the sample analyzer in a modification of the present invention.

DETAILED DESCRIPTION OF THE PREFERRED EMBODIMENTS

Hereinafter, an embodiment of a sample analyzer and a sample analyzing method of the present invention will be described in detail with reference to the accompanying drawings. It should be noted that in the present embodiment, a "reagent set" means a combination of reagent lots.

Figure 2:
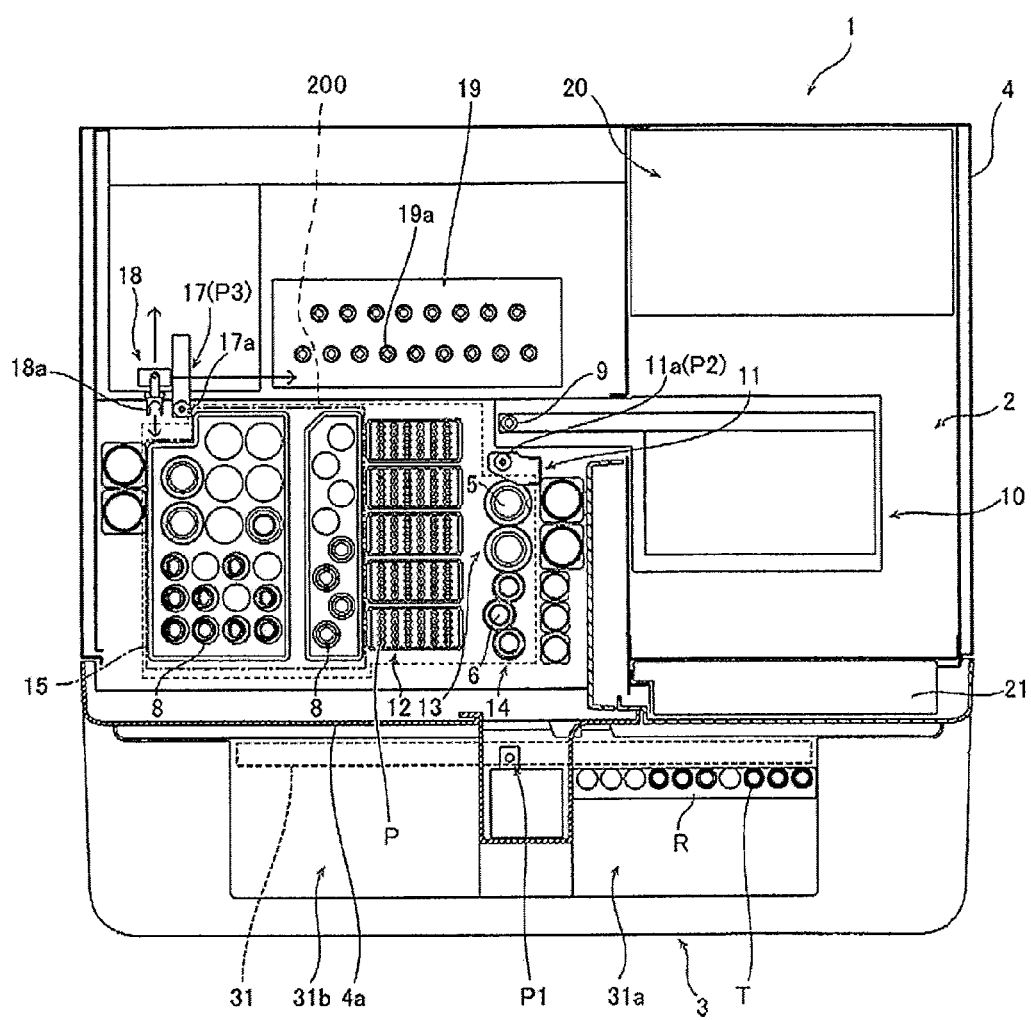
FIG. 2 is a schematic plan view of the sample analyzer shown in FIG. 1.

FIG. 1 is a perspective view of a sample analyzer 1 according to one embodiment of the present invention, and FIG. 2 is a schematic plan view of the sample analyzer 1 shown in FIG. 1. The sample analyzer 1 includes a reagent storage 200 capable of holding a plurality of reagents, and is an apparatus that can measure a sample by use of a plurality of kinds of reagents in combination. More specifically, the sample analyzer 1 is a blood coagulation analyzer capable of measuring multi-items. The sample analyzer 1 uses a plurality of kinds of reagents in combination to measure plasma as a sample, thereby obtaining physical measurement data such as reaction time and turbidity, and applies the measurement data to a calibration curve, thereby converting the measurement data into an analysis parameter regarding the amount of a coagulation factor of the sample or the coagulation activity thereof.

[Overall Structure of Analyzer]

First, the overall structure of the sample analyzer 1 will be described with reference to FIGS. 1 and 2.

As shown in FIG. 1, the sample analyzer 1 includes a measurement apparatus 2 as a measurement unit, and a transport apparatus 3 arranged to the front face side of the measurement apparatus 2. The measurement apparatus 2 is housed in a housing 4.

The measurement apparatus 2 has a function of measuring a specimen prepared by mixing a sample collected from a subject and a reagent. As shown in FIG. 2, the measurement apparatus 2 includes a cuvette supplying part 10, a sample dispenser 11, a sample plate placement part 12, container setting parts 13 to 15, a reagent dispenser 17, a cuvette transfer part 18, a detection part 19, a controller 20, and a display part 21.

The measurement apparatus 2 is configured to perform optical measurement on a specimen prepared from a sample supplied from the transport apparatus 3, so as to be able to obtain optical information regarding the sample. In the sample analyzer 1 according to the present embodiment, optical measurement is performed on a sample that has been dispensed into a cuvette 9 in the measurement apparatus 2 from a sample container T in the transport apparatus 3.

The cuvette supplying part 10 contains a plurality of cuvettes 9 and is configured to be able to sequentially supply cuvettes 9, one by one, to a predetermined position.

The sample dispenser 11 includes a pipette 11a which aspirates and discharges a sample, and is configured to be movable in a predetermined region including a sample aspirating position P1 and a sample dispensing position P2 by means of a movement mechanism not shown. The sample dispenser 11 aspirates, from a sample container T transported to the sample aspirating position P1 on a transport path 31 of the transport apparatus 3, a sample contained in the sample container T. Then, the sample dispenser 11 dispenses the sample into a well in a sample plate P placed on the sample plate placement part 12. Moreover, the sample dispenser 11 can aspirate a cleaning solution from a cleaning solution container 5 set in the container setting part 13 and a diluent from a diluent container 6 set in the container setting part 14, and dispense them.

On the sample plate placement part 12, the sample plates P each having a plurality of wells are arranged, adjacent to each other. Into a well of a sample plate P, the sample aspirated by the sample dispenser 11 is dispensed (this will be referred to as primary dispensing). The sample primarily dispensed into the well is aspirated by the sample dispenser 11 again at the time of measurement, to be dispensed (this will be referred to as secondary dispensing) into a cuvette 9 held by the cuvette transfer part 18.

In the measurement apparatus 2, the container setting parts 13 and 14 are arranged in a middle portion in the width direction of the apparatus, and the container setting part 15 is arranged in a left portion when viewed from the front face (lid 4a side) of the sample analyzer 1. Various reagent containers set in the container setting parts 13 to 15 are set with their caps removed.

The reagent dispenser 17 includes a pipette 17a for dispensing a reagent, and is configured to be movable in a region including the space above the container setting part 15 (Z1 direction) and a reagent dispensing position P3 by means of a movement mechanism not shown. The reagent dispenser 17 is configured to aspirate, by use of the pipette 17a, a reagent from a reagent container 8 being a target of the dispensing, and to dispense the reagent into a cuvette 9 disposed at the reagent dispensing position P3.

The cuvette transfer part 18 takes out a cuvette 9 supplied by the cuvette supplying part 10, and transfers the cuvette 9 to the sample dispensing position P2, the reagent dispensing position P3, or other parts such as the detection part 19. The cuvette transfer part 18 includes a catcher 18a capable of gripping and transferring a cuvette 9. By moving the catcher 18a by means of a movement mechanism not shown, the cuvette transfer part 18 takes out and places a cuvette 9, and also performs agitation and the like of a sample and a reagent in a cuvette 9.

The detection part 19 has a function of heating a mixture solution (measurement specimen) prepared by adding a reagent to a sample, and of performing optical measurement on the measurement specimen. The detection part 19 has a plurality of cuvette setting holes 19a in each of which a cuvette 9 can be inserted to be set. The specimen in a cuvette 9 set in a cuvette setting hole 19a is heated to a predetermined temperature by a heating mechanism not shown, whereby reaction between the sample and the reagent proceeds. The detection part 19 is configured such that measurement light introduced via an optical fiber from a light source (not shown) is emitted to a specimen in the cuvette setting hole 19a. The detection part 19 includes a light receiving element (not shown) which receives light emitted to the specimen, and detects light received by the light receiving element, to output a detection signal corresponding to the amount of the received light.

The obtained detection signal is outputted to the controller 20. The controller 20 obtains measurement data such as reaction time and turbidity based on the obtained detection signal. Moreover, the controller 20 has a function of displaying various screens including an analysis result in the display part 21 arranged at the front face of the housing 4, and of controlling operation of components of the measurement apparatus 2 and the transport apparatus 3.

The transport apparatus 3 is configured to transport, to the sample aspirating position P1, a rack R on which a plurality of (10 at maximum in the present embodiment) sample containers T each containing a sample are set, thereby supplying the samples to the measurement apparatus 2. The transport apparatus 3 includes the transport path 31 along which the rack R is transported to the measurement apparatus 2.

The transport path 31 is provided so as to extend sideways, and connects a rack supplying part 31a to a rack storage part 31b. The rack R holding sample containers T is set in the rack supplying part 31a. The rack supplying part 31a sequentially supplies the set rack R to the transport path 31. The transport path 31 transports the rack R supplied from the rack supplying part 31a toward the sample aspirating position P1. The transport path 31 locates, at the sample aspirating position P1, a sample container T set in the sample rack R, one by one from the head in order, and the sample dispenser 11 aspirates the sample from the sample container T located at the sample aspirating position P1. When this cycle is performed for all the sample containers T, the transport path 31 transports the rack R toward the rack storage part 31b. The rack storage part 31b receives, from the transport path 31, the rack R holding the sample containers T from which the samples have been aspirated, and stores the rack R therein.

The reagent storage 200 includes the container setting part 15 capable of holding a plurality of reagents. In order to avoid suspension of measurement due to occurrence of reagent shortage during continuous measurement, the sample analyzer 1 according to the present embodiment has a function of automatic reagent switching, in which a spare reagent vial of the same kind of the reagent being used is set in advance in the container setting part 15, whereby the reagent being used in sample measurement is automatically switched to a reagent of another reagent vial of the same kind, to continue the measurement.

With respect to the sample analyzer 1 according to the present embodiment, there are cases where, for one measurement item, a sample is measured by use of a plurality of kinds of reagents held in the container setting part 15 in combination. For example, in the case of APTT being a representative measurement item of a blood coagulation test, an APTT reagent is added to plasma being a sample, the mixture is heated for a several minutes, then a calcium chloride solution is added to the mixture, and reaction in the mixture solution is measured by photometry. That is, two kinds of reagents are used for one measurement item. In the case of D-dimer being one item of a blood coagulation test, in one measurement protocol, three kinds of reagents, i.e., a diluent, a D-dimer buffer, and a latex reagent, are used.

As in the example described above, with respect to a measurement item for which a plurality of kinds, i.e., two or more, of reagents are used, a calibration curve needs to be created for each combination of reagent lots. For example, it is assumed that there is a certain measurement item for which three kinds of reagents, i.e., R1, R2, and R3, are used. In this case, when the reagent R3 is switched to a reagent R3' of a different lot, a calibration curve needs to be created for a reagent set "R1, R2, and R3'". Similarly, a new calibration curve needs to be created also in a case where, for example, the reagent R2 is switched to a reagent R2' of a different lot. Further, also with respect to another measurement item for which a plurality of kinds of reagents are used, every time a reagent lot is switched, a calibration curve needs to be created for the new reagent lot set.

Normally, a calibration curve is created in advance prior to a routine test, in anticipation of shortage of a reagent. However, when an operator forgets to create in advance a calibration curve or when orders by a number greater than expected by the operator are concentrated to one measurement item, there are cases where, due to the function of automatic reagent switching, a reagent set is switched to another reagent set for which no calibration curve has been created, and then measurement of a sample is performed. In this case, since no calibration curve applicable to the sample is stored in the analyzer, only measurement data is stored and analysis is not performed. Thus, in order to analyze the measurement data by use of a calibration curve to obtain an analysis parameter, it is necessary to create a calibration curve by use of the same reagent set after the measurement has ended, to apply the measurement data to the calibration curve, and then, to recalculate an analysis parameter. When ordering creation of a calibration curve to the analyzer, the operator prepares a specimen for calibration curve creation (calibrator), designates a reagent set for which a calibration curve is to be created, inputs a calibration curve creation order to the analyzer, and causes the analyzer to execute measurement of the calibrator in accordance with the calibration curve creation order.

As a function to support the operator in inputting a calibration curve creation order, the sample analyzer 1 has a function of presenting combinations conceivable as combinations of reagents set and registered in the analyzer. More specifically, the sample analyzer 1 has a function of, upon designation of a measurement item for which creation of a calibration curve is required, extracting all combinations conceivable as combinations of reagents to be used for the measurement item, and displaying a list of the extracted combinations in the display part 21. It is sufficient for the operator to select a reagent set for which a calibration curve is to be created, from the displayed reagent sets.

However, normally, a calibration curve is created for a reagent set not used in sample measurement (i.e., a reagent set that is going to be used). Therefore, most of the displayed combinations of reagents are reagent sets unused in sample measurement. When measurement of a sample has been performed by use of a reagent set without a calibration curve due to automatic reagent switching, unused reagent sets and reagent sets that were already used in sample measurement but for which no calibration curve has been created are mixed, and thus, the operator needs to find the reagent set that was already used in sample measurement from among many unused reagent sets.

This work may become complicated, in particular, for a measurement item for which a plurality of reagents are used. For example, it is assumed that there is a measurement item for which three kinds of reagents, R1, R2, and R3, are used. When spare reagents (R1', R2', and R3') are set for R1, R2, and R3, respectively, the number of the conceivable reagent sets is $2^3=8$. Among these combinations, from seven combinations excluding the combination of R1, R2, and R3 for which a calibration curve has already been created, the operator needs to designate a combination of reagents that was used in sample measurement due to the automatic reagent switching, and that is to be used in recalculation. This work is inconvenient for the operator because the operator has to know the lots of the reagents used as a result of the automatic reagent switching.

Thus, in the present embodiment, in a case where as a result of automatic reagent switching, measurement of a sample has been performed by use of a reagent set for which no calibration curve has been stored, the controller 20 stores measurement data obtained by the measurement, adds, to the used reagent set, information indicating that the reagent set that was used in the sample measurement was used without a calibration curve, and stores the reagent set. Then, when displaying candidates for reagent sets for each of which a calibration curve can be created, the controller 20 automatically extracts the reagent set used in the sample measurement without a calibration curve, based on the information added to the reagent set, and displays the extracted reagent set in the display part 21 together with indication that a calibration curve needs to be created for calculation of an analysis parameter of the sample. Accordingly, the operator need not select the combination of the reagent lots used due to automatic reagent switching from among many combinations of reagent lots, and can advance the work smoothly.

[Configuration of Controller]

Figure 3:
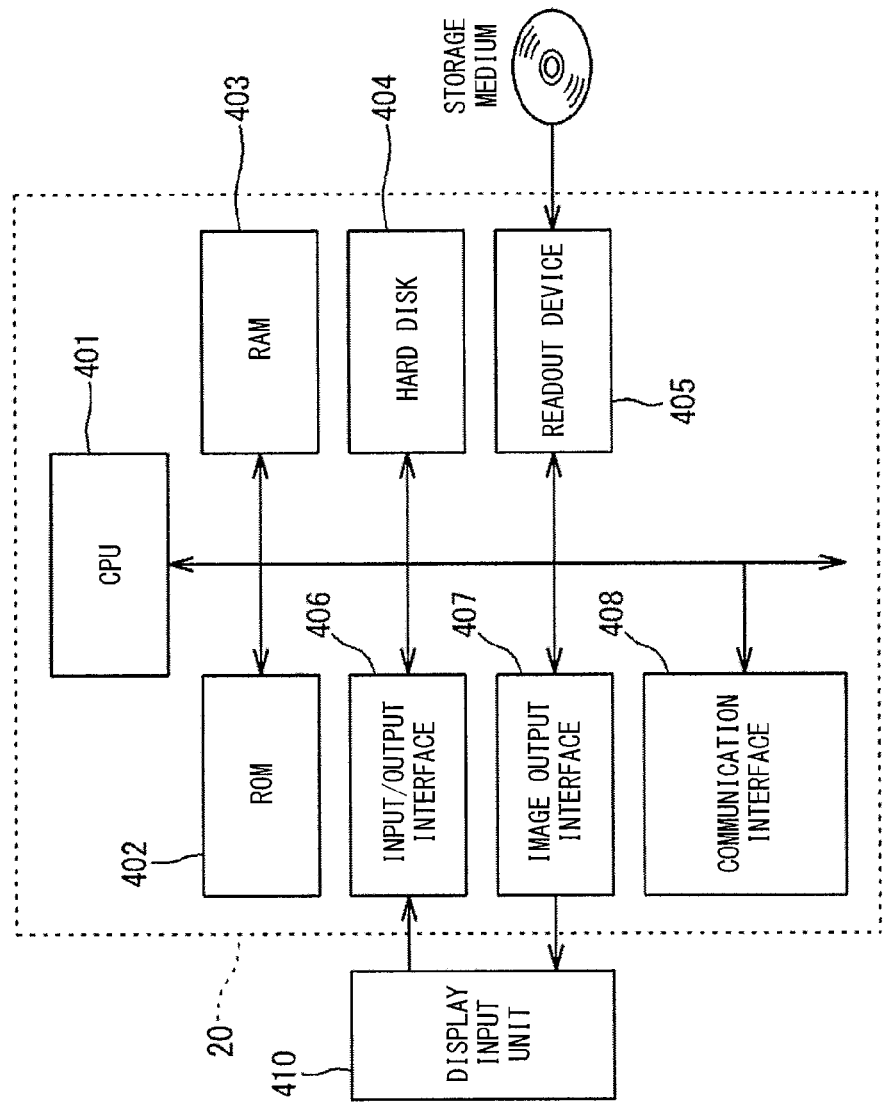
FIG. 3 shows a configuration of a controller in the sample analyzer.

FIG. 3 shows a configuration of the controller 20 in the sample analyzer 1.

The controller 20 is implemented by a personal computer, and includes a body 400 and a display input unit 410. The body 400 includes a CPU 401, a ROM 402, a RAM 403, a hard disk 404, a readout device 405, an input/output interface 406, an image output interface 407, and a communication interface 408.

The CPU 401 executes computer programs stored in the ROM 402, and computer programs loaded onto the RAM 403. The RAM 403 is used for reading out computer programs stored in the ROM 402 and the hard disk 404. The RAM 403 is also used as a work area for the CPU 401 when the CPU 401 executes computer programs.

The hard disk 404 has installed therein various computer programs to be executed by the CPU 401 and data to be used in the execution of the computer programs, such as an operating system and application programs.

The readout device 405 is implemented by a CD drive, a DVD drive, or the like, and can read out computer programs and data stored in a storage medium.

The input/output interface 406 receives a signal outputted from the display input unit 410. The image output interface 407 outputs an image signal corresponding to an image data to the display input unit 410. The display input unit 410 displays an image based on the image signal outputted from the image output interface 407, and outputs, to the input/output interface 406, an instruction received from a user via a screen of the display input unit 410.

[Sample Analysis Flow]

Figure 4:
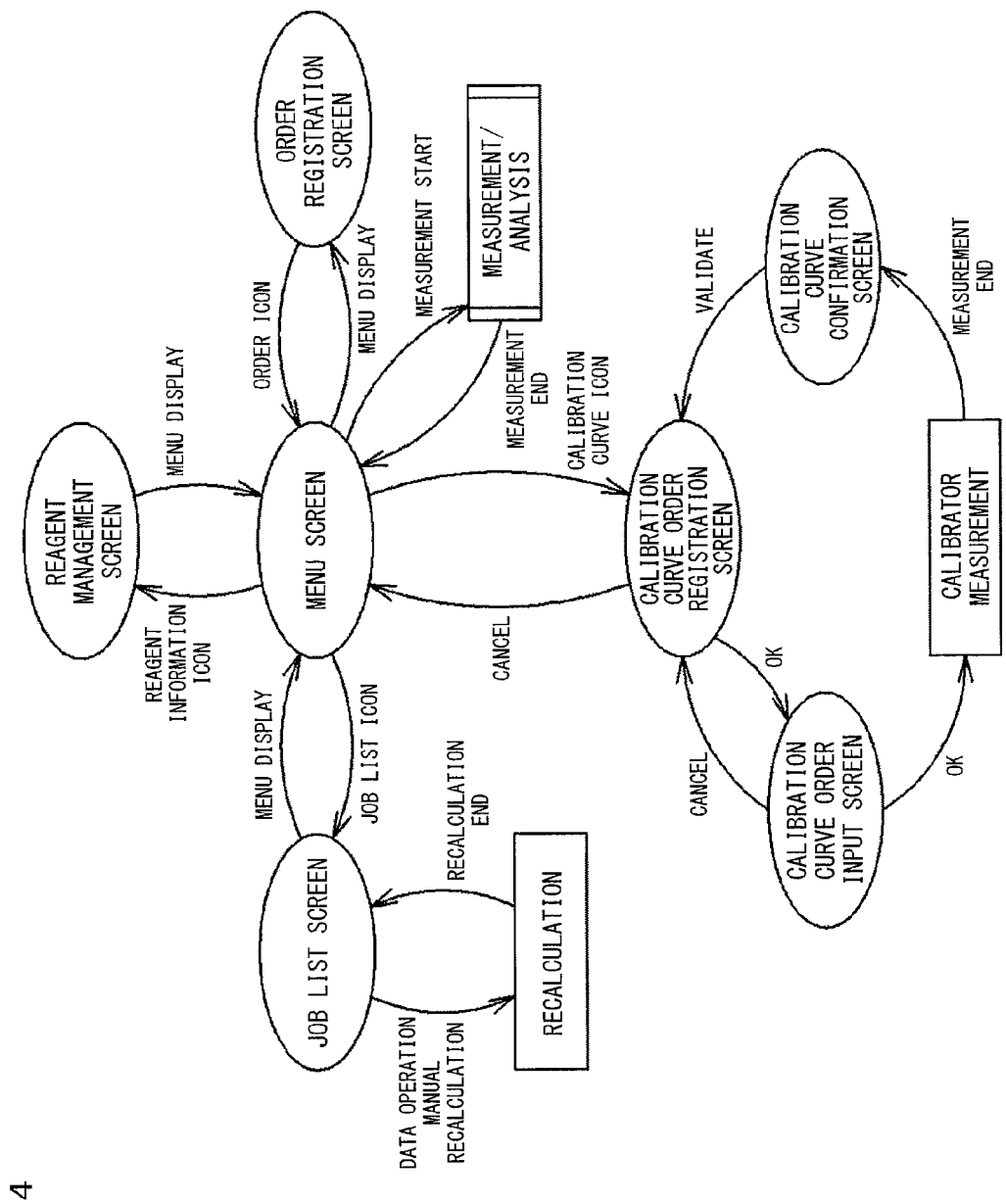
FIG. 4 is a diagram showing shifts among states of the sample analyzer according to one embodiment of the present invention.
Figure 5:
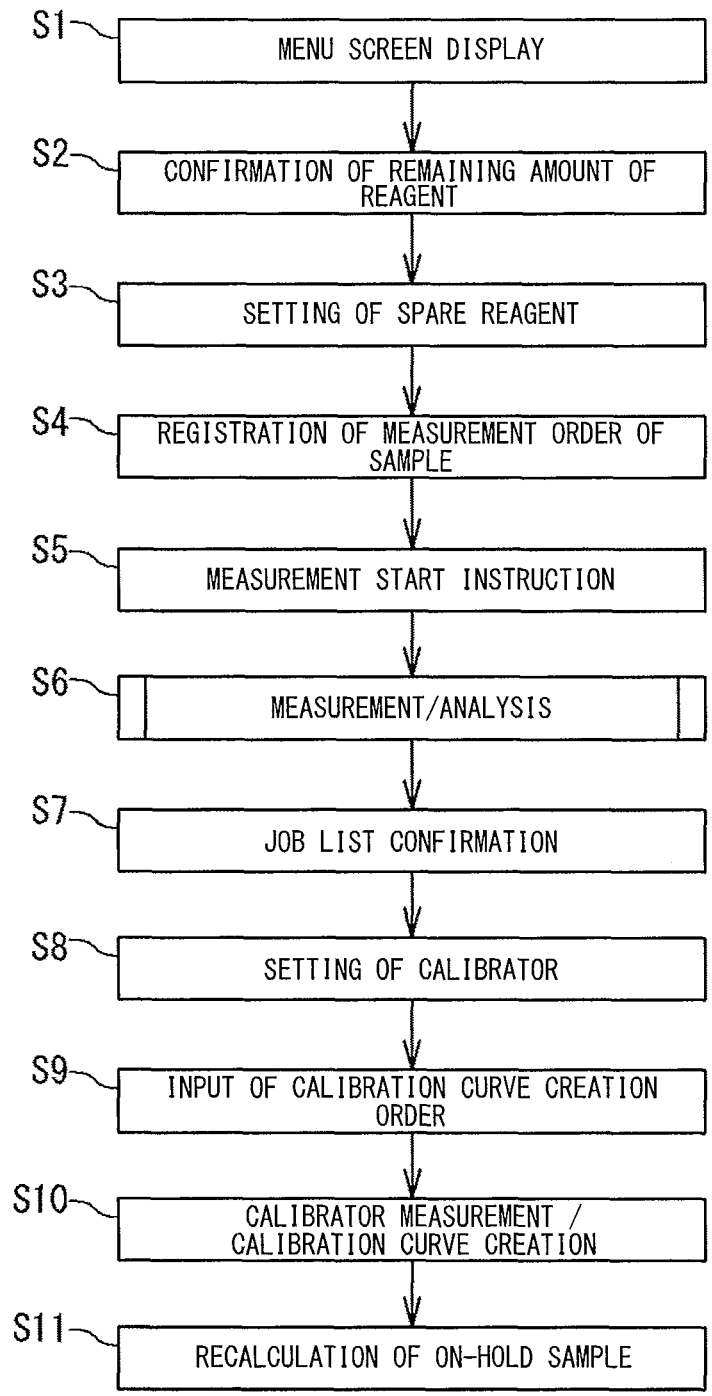
FIG. 5 is a flow chart showing a flow of operation of the sample analyzer according to one embodiment of the present invention.

Next, one example of a sample analysis flow using the sample analyzer 1 above will be described. FIG. 4 is a diagram showing shifts among states of the sample analyzer 1 according to one embodiment of the present invention. FIG. 5 is a flow chart showing a flow of operation of the sample analyzer according to one embodiment of the present invention.

As described above, the sample analyzer 1 has a function of, upon occurrence of reagent shortage during continuous measurement, automatically shifting to measurement that uses a reagent of a new lot, thereby continuing the continuous measurement. Hereinafter, this function of the sample analyzer 1 will be referred to as "automatic reagent switching". Further, performing measurement of a sample by use of a reagent set for which no calibration curve has been created due to automatic reagent switching will be referred to as "on-hold measurement", and a sample for which calculation of an analysis parameter has not been completed due to the on-hold measurement will also be referred to as an "on-hold sample". In contract to this, a calibration curve is created in advance prior to start of measurement, and performing measurement of a sample by use of the calibration curve that has been validated will also be referred to as "normal measurement". In the following, operation of the sample analyzer 1 in each step in the work flow shown in FIG. 5 will be described with reference to the diagram showing shifts among states in FIG. 4.

[S1: Menu Screen Display]

Figure 6:
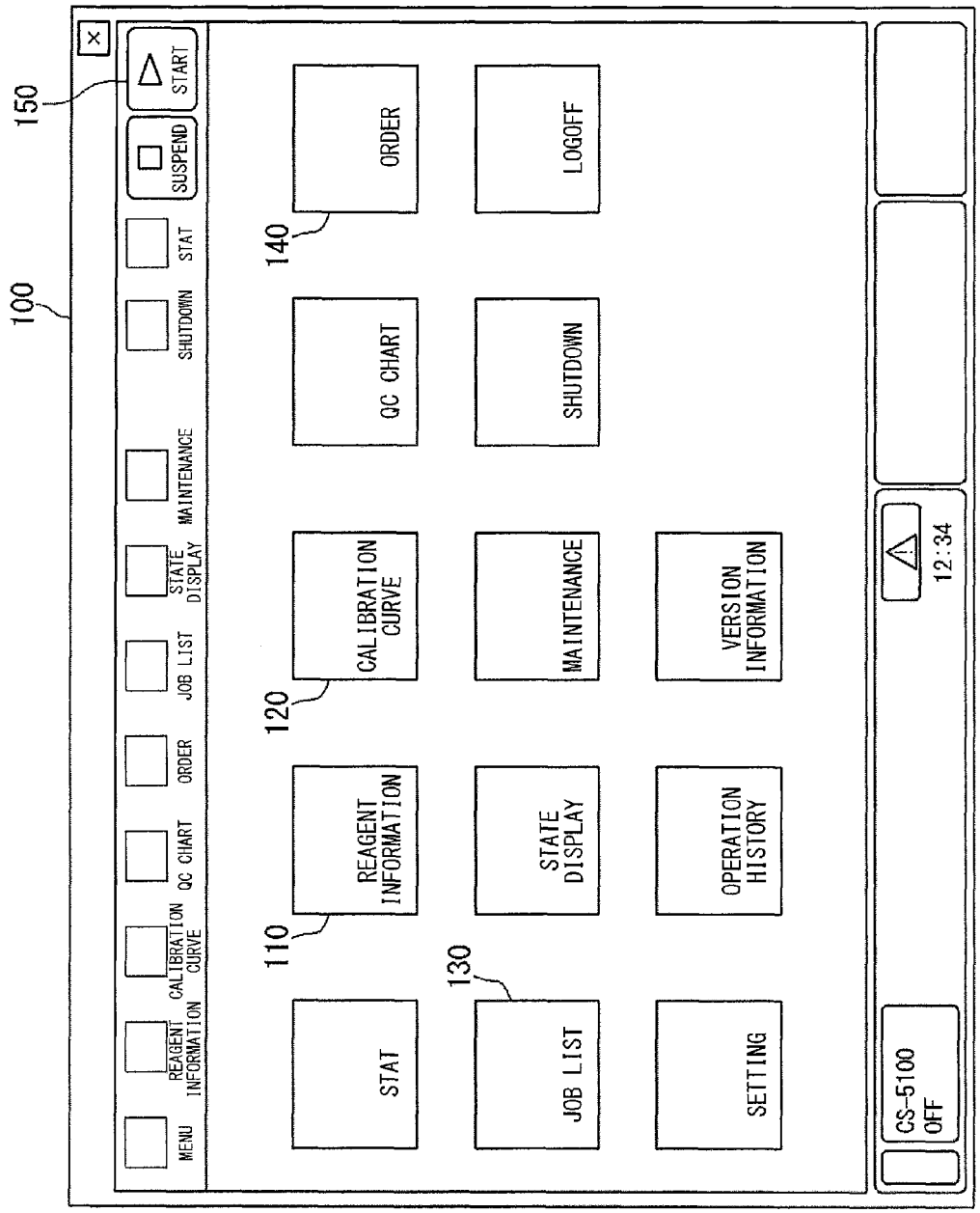
FIG. 6 shows one example of a menu screen.

Upon activation of the sample analyzer 1, various drive units such as the sample dispenser 11 and programs stored in the controller 20 are initialized, and then, a menu screen 100 shown in FIG. 6 is displayed. On the menu screen, a plurality of icons each functioning as a short-cut to a main function screen are displayed. A reagent information icon 110 is a short-cut to a reagent management screen 40 (see FIG. 7). A calibration curve icon 120 is a short-cut to a calibration curve order registration screen 50 (see FIG. 11).

Figure 8:
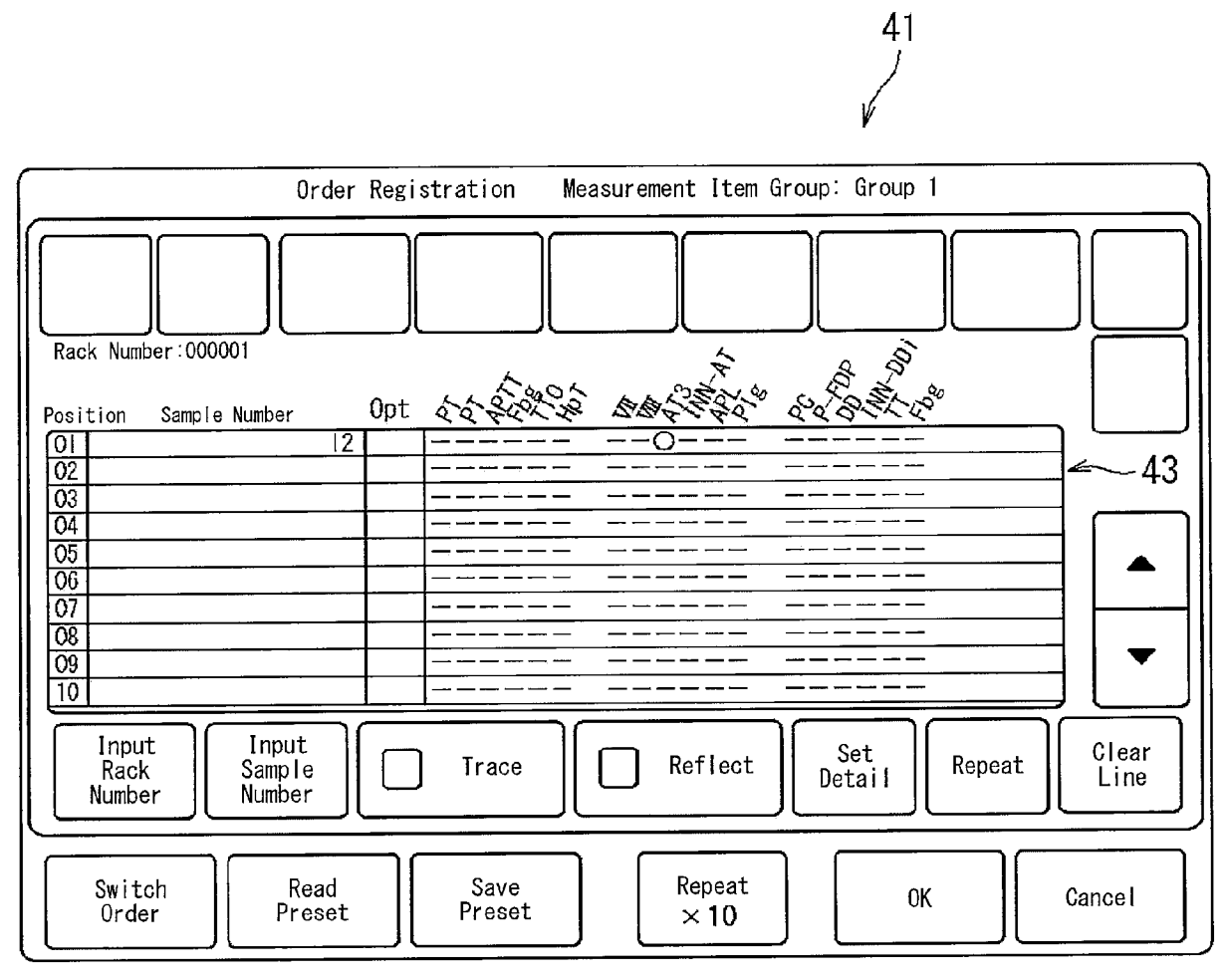

A job list icon 130 is a short-cut to a job list screen 46 (see FIG. 10). An order icon 140 is a short-cut to an order registration screen 41 (see FIG. 8). The operator selects an icon of a desired function on the menu screen to display a desired function screen, so as to operate the sample analyzer 1.

[S2: Confirmation of Remaining Amount of Reagent]

Figure 7:
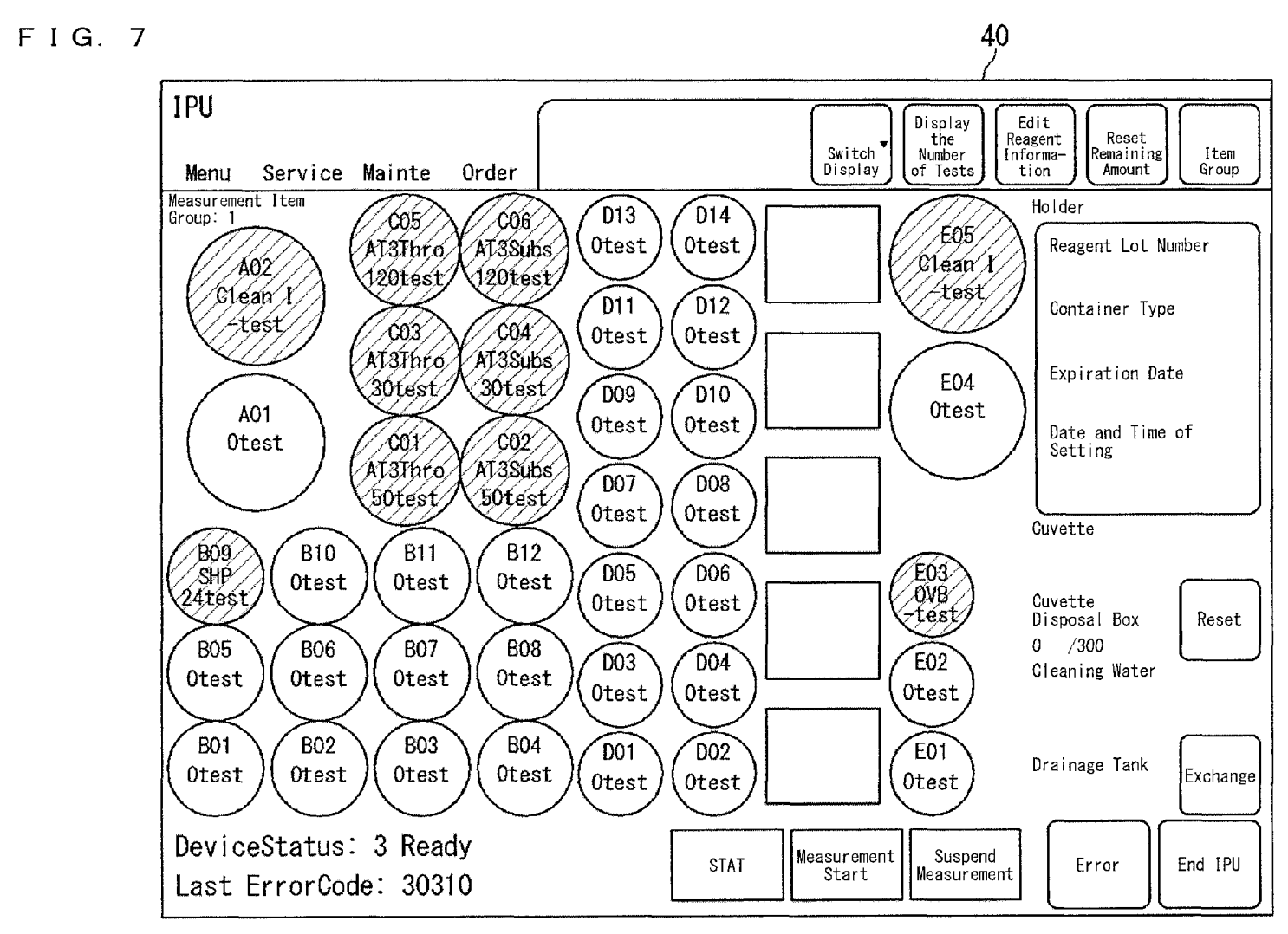

Upon the reagent information icon 110 being operated on the menu screen 100, the reagent management screen 40 shown in FIG. 7 is displayed in the display part 21. On the reagent management screen 40, arrangement of holding positions in the reagent storage 200 including the container setting part 15 is schematically displayed, and information (measurement item, reagent name, and the number of remaining tests) of the reagent container held in each holding position is displayed in association with its holding position. For example, it is shown that: at a holding position C05, a "Thro" reagent to be used for measurement item "AT3" is held, and the number of remaining tests is 120. The operator refers to the reagent management screen 40 (see FIG. 7) displayed in the display part 21, and determines whether replenishment of a reagent is necessary for performing continuous measurement.

[S3: Setting of Spare Reagent]

When replenishment is necessary, the operator prepares a spare reagent, causes the barcode attached to the reagent to be read, and the like, registers the information (measurement item, reagent lot, the number of remaining tests, and the like) of the reagent into the sample analyzer 1, and sets the reagent container in the container setting part 15 of the reagent storage 200. When the reagent information is registered and the reagent container is set, information of the reagent management screen 40 is updated.

There may be a case where the spare reagent and the reagent being used is of the same lot, but here, in order to facilitate description, it is assumed that the spare reagent and the reagent being used are of different lots, respectively. Moreover, it is assumed that, for the reagent being used, a calibration curve has already been created and validated.

[S4: Registration of Measurement Order of Sample]

When "menu" has been selected from the tool bar on the reagent management screen 40, the screen shifts to the menu screen 100. The operator operates the order icon 140 on the menu screen 100, to cause the order registration screen 41 shown in FIG. 8 to be displayed in the display part 21. The operator inputs a measurement order of each sample via the screen displayed in the display part 21. On the order registration screen 41, at least a sample number and a measurement item are inputted. When the OK button is operated, the order is registered, and the screen shifts to the menu screen 100.

[S5: Measurement Start Instruction]

The operator operates a start button 150 on the menu screen 100, and causes the analyzer to start measurement/analysis on the sample for which the measurement order has been registered.

[S6: Measurement/Analysis]

Upon the start button 150 being operated, a measurement start instruction is inputted to the controller 20. When the controller 20 receives the measurement start instruction, measurement/analysis of the sample is started.

Figure 9:
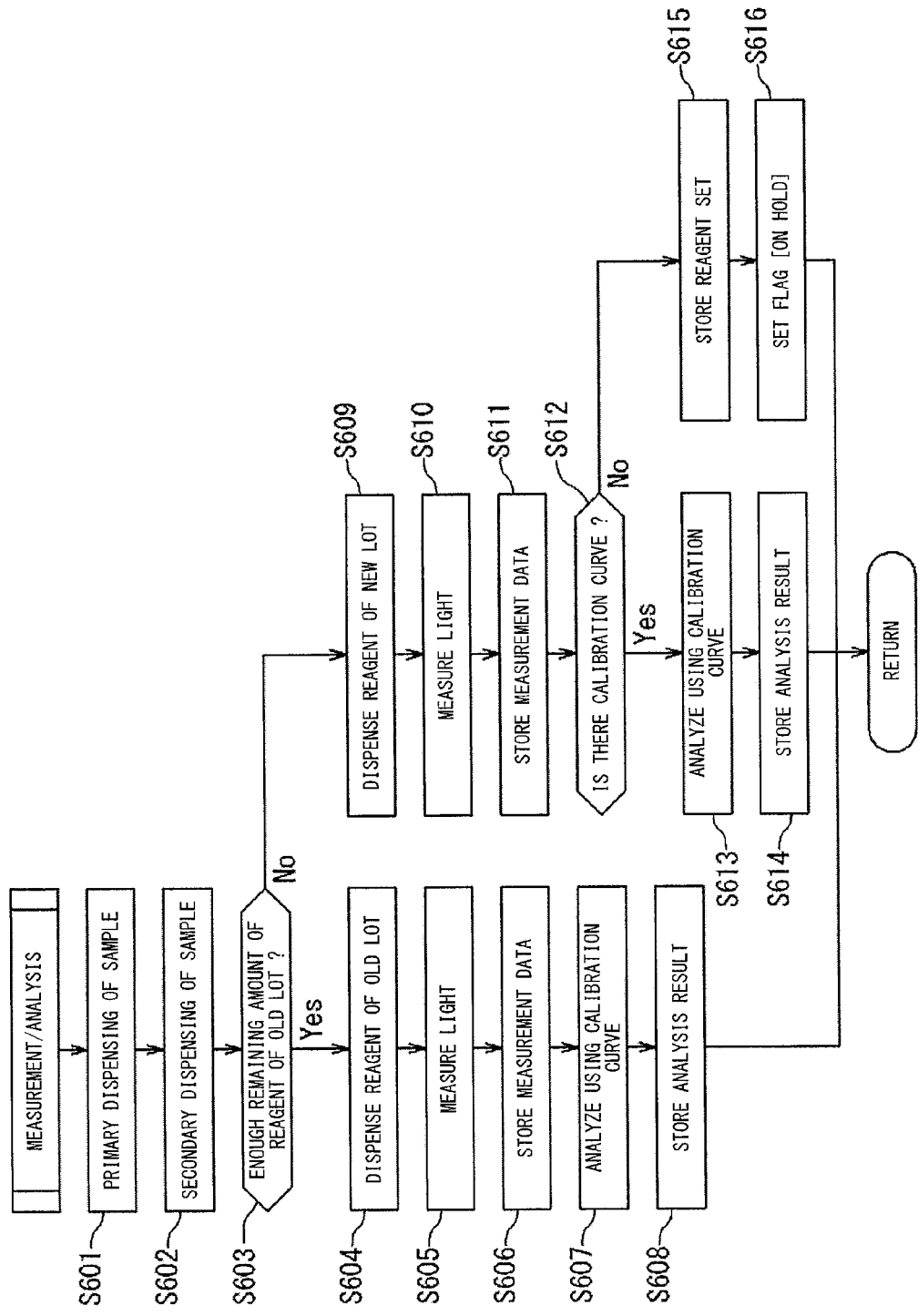
FIG. 9 is a flow chart showing a flow of operation of measurement/analysis performed by the sample analyzer.

FIG. 9 is a flow chart showing a flow of operation of measurement/analysis performed by the sample analyzer 1.

In step S601, the sample dispenser 11 aspirates the sample from a sample container T transported by the transport apparatus 3 and dispenses the sample into a well of the sample plate P (primary dispensing). Then, in step S602, the sample dispenser 11 dispenses a part of the sample dispensed in the well into a cuvette 9 (secondary dispensing).

In step S603, the controller 20 determines, with respect to the measurement item ordered for the dispensed sample, whether the number of remaining tests of each reagent container being used is 0. When the number of remaining tests is not 0 (Yes in S603), the reagent dispenser 17 aspirates the reagent from each reagent container being used and dispenses the reagent into the cuvette 9 (step S604). The cuvette 9 into which the sample and the reagents have been dispensed is transferred by the cuvette transfer part 18 to the detection part 19, to be subjected to optical measurement of the sample in the detection part 19 (step S605). Measurement data obtained through the measurement is outputted to the controller 20, and the controller 20 stores, in the hard disk 404, the measurement data together with the lot information of the reagent set used in the measurement (step S607). The controller 20 applies the measurement data stored in S606 to its corresponding calibration curve, and calculates an analysis parameter. For example, when the measurement item AT3 has been measured, an optical property value "dOD/min" which depends on time is obtained as the measurement data, and this value is applied to the calibration curve, whereby "AT3(%)" indicating the activity of AT3 is calculated as the analysis parameter. The controller 20 stores the calculated analysis parameter in the hard disk 404 (step S608), and then ends the processing of the measurement/analysis.

In S603, when the number of remaining tests of a reagent being used has become 0, the controller 20 executes automatic reagent switching. Specifically, in step S609, the reagent dispenser 17 stops dispensing the reagent from the reagent container being used for which the number of remaining tests has become 0, and aspirates a reagent from a reagent container of a new lot to dispense it into the cuvette 9. Thereafter, optical measurement is performed in the same manner as in the operation in the normal time (S605, S606), and measurement data is stored in the hard disk 404 together with the lot information of the reagent set used in the measurement (S610, S611).

Next, the controller 20 determines whether there is a calibration curve corresponding to the reagent set including the reagent of the new lot (step S612).

As described later, upon creating a calibration curve, the controller 20 stores, into the hard disk 404, the created calibration curve together with the information (the lot number of each reagent) of the reagent set used in the creation of the calibration curve. Furthermore, when the created calibration curve has been validated, information indicating that the calibration curve has been validated is added to the calibration curve.

The controller 20 determines whether a validated calibration curve corresponding to the reagent set including the reagent of the new lot used in the measurement is stored in the hard disk 404. When the corresponding calibration curve is stored and the calibration curve has been validated (Yes in S612), the controller 20 applies the measurement data to the stored validated calibration curve to calculate an analysis parameter (S613), stores the calculated analysis parameter into the hard disk 404 (S614), and then ends processing of the measurement/analysis.

On the other hand, in a case where no validated calibration curve corresponding to the reagent set including the reagent of the new lot has been stored (No in S612), the controller 20 adds information of "with On Hold" to status information of the reagent set (S615). Further, the controller 20 adds a flag "On Hold" to job information indicating the state of the measurement order of the sample (S616), and then ends the processing of the measurement/analysis.

[S7: Job List Confirmation]

With reference back to FIG. 5, in order to confirm an analysis result, the operator operates the job list icon 130 to cause the job list screen 46 to be displayed in the display part 21. FIG. 10 shows an example of the job list screen. On the job list screen 46, a list of samples for which measurement orders have been inputted is displayed. In the state shown, in each line, sample information of the individual sample is displayed. By switching between the tabs at the lower left of the screen, the operator can switch the display content, and can confirm the result of measurement/analysis of each sample. The operator confirms the result of measurement/analysis of the sample, and when there is no problem, presses a "validate" button provided in an upper portion of the job list screen, to validate the result. In the leftmost column of the line of the validated sample, a display "v" indicating that the result has been validated is added.

The operator confirms the job list screen 46 and determines whether there is an on-hold sample. In the column "measurement state" in the list, information indicating the progress of measurement of each sample is displayed. "Complete" is displayed when measurement and analysis of all measurement items ordered for the sample have ended normally. On the other hand, in a case where measurement of all the ordered measurement items has been ended, but there is a measurement item for which analysis has not been completed due to lack of a validated calibration curve, "On Hold" is displayed. This display is added to a sample for which the flag "On Hold" has been set in S616 in FIG. 9. In the screen example shown in FIG. 10, the measurement state of the sample whose sample number is 12 is being displayed as "On Hold".

[S8: Setting of Calibrator]

When there is a sample whose measurement state is "On Hold" on the job list screen 46, it is necessary to perform calibration for the reagent set used in the measurement of that sample. In order to create a calibration curve for the reagent set including a reagent of a new lot used in the measurement of the on-hold sample, the operator sets a rack R holding a calibrator in the transport apparatus 3.

[S9: Input of Calibration Curve Creation Order]

Next, the operator inputs a calibration curve creation order, using the reagent set used in the measurement of the on-hold sample as the target for creating a calibration curve. When the calibration curve icon 120 is selected on the menu screen 100, a calibration curve order registration screen shown in FIG. 11 is displayed.

Figure 11:
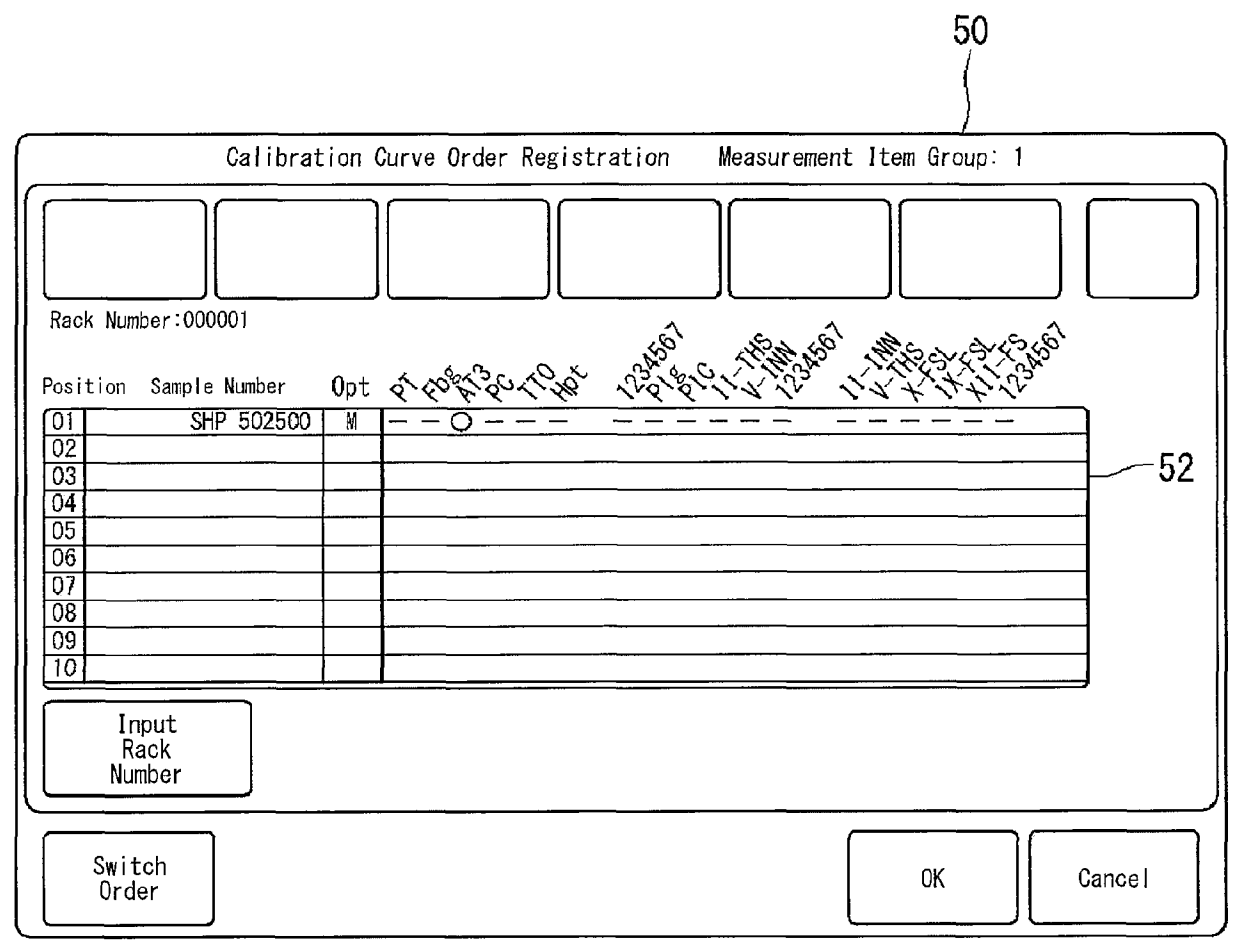

On the calibration curve order registration screen 50 shown in FIG. 11, a region 52 is arranged in a middle portion of the screen, the region 52 being for displaying a list of the sample number of a calibrator and a measurement item for which measurement of the calibrator is requested. The operator selects the column of the sample number, inputs the sample number of the calibrator, and selects, in the column of the measurement item, the position corresponding to the desired measurement item, thereby inputting the measurement item for which measurement of the calibrator is requested, that is, the measurement item for which analysis has not been completed for the sample displayed as "On Hold" on the job list screen 46. In the example shown, with respect to the calibrator "SHP 502500", a measurement request for measurement item "AT3" has been inputted.

Figure 12:
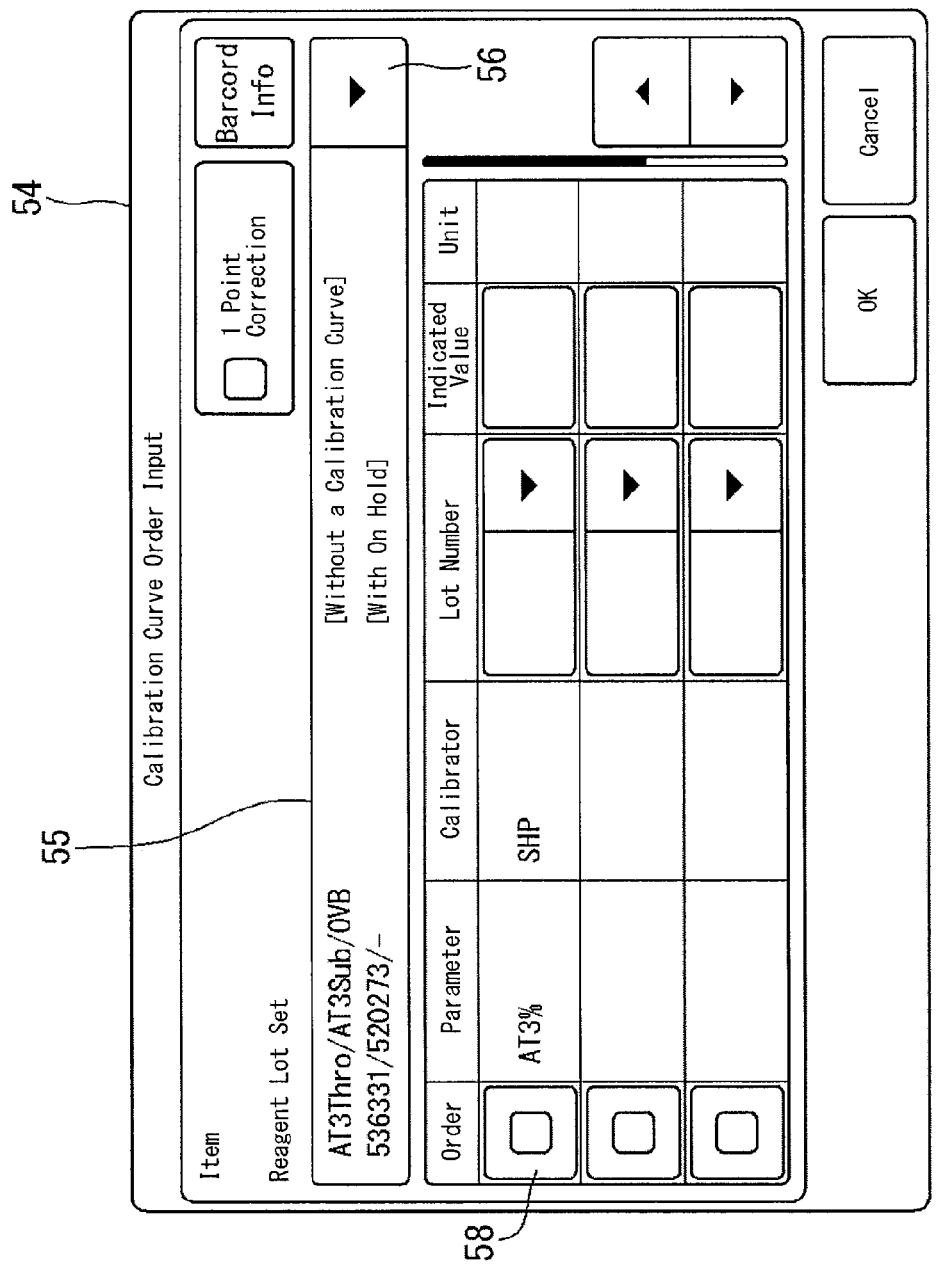
FIG. 12 shows one example of a calibration curve order input screen.

When the OK button in FIG. 11 is pressed, a calibration curve order input screen 54 shown in FIG. 12 is displayed in the display part 21. FIG. 12 shows an initial screen of the calibration curve order input screen 54.

The calibration curve order input screen 54 includes a designation region 55 for designating a reagent set being a calibration curve creation target. In the designation region 55, a combination of lot numbers of the reagent set designated by the operator as the calibration curve creation target, and the status information of the reagent set are displayed. When the OK button has been operated, the designated reagent set displayed in the designation region 55 is subjected to measurement as a calibration execute target, whereby a calibration curve is created.

In the example shown, the reagent set displayed as default in the designation region 55 includes a reagent "AT3Thro" whose lot number is "536331", a reagent "AT3Sub" whose lot number is "520273", and a reagent OVB (without lot number). Then, according to the status information of the designation region 55, this reagent set has been used in measurement of an on-hold sample, and no calibration curve has been created.

On the calibration curve order input screen 54, next to the designation region 55, a pull-down button 56 is provided. Upon operation of the pull-down button 56, a pull-down menu 57 shown in FIG. 13 is displayed. In the pull-down menu 57, a list of combinations of lots of reagents usable for the measurement item designated on the calibration curve order registration screen in FIG. 11 is displayed. In the example shown, as the combination of lots of a first reagent "AT3Thro", a second reagent "AT3Sub", and a buffer "OVB" to be used for measurement item AT3, all combinations of lots conceivable within combinations of lots present in the reagent storage 200 are displayed. In the screen example of FIG. 13, the uppermost part of the pull-down menu 57 is being displayed. Although not shown, by pressing the scroll button next to the menu, it is possible to scroll down the menu.

When the operator has selected one reagent set from among a plurality of reagent sets displayed in the pull-down menu 57, the reagent set having been displayed in the designation region 55 is replaced with the selected reagent set. That is, the reagent set selected in the pull-down menu 57 is displayed in the designation region 55, and the reagent set having been displayed in the designation region 55 is moved to the pull-down menu 57. Accordingly, the operator can select as desired the reagent set being the calibration curve creation target from the pull-down menu 57.

Each line of the pull-down menu 57 corresponds to a reagent set. Each line includes, as in the display of the designation region 55 in FIG. 12, the lot number of each reagent included in the combination, and the status information of the reagent set.

In the example shown, the status information is arranged from the uppermost line in the pull-down menu 57 in the order of: "with a new calibration curve" and "with On Hold"; "without a calibration curve"; "with a new calibration curve"; and "with a validated calibration curve".

In the designation region 55 of the calibration curve order input screen 54, a reagent set having highest display priority is displayed as default. On the other hand, in the pull-down menu 57, a reagent set having second highest priority is displayed in the uppermost line, thereafter, reagent sets are displayed in accordance with their priority. The display priority is set such that among reagent sets that could be targets for calibration curve measurement, a reagent set having higher urgency ranks in a higher order. In the present embodiment, the priority of a reagent set including the status information of "with On Hold" is set to be highest. Accordingly, in a case where there is a reagent set used in measurement of a sample without a calibration curve, that reagent set is displayed with the highest priority.

The status information of a reagent set includes attribute information regarding the presence/absence of "On Hold" (hereinafter, first attribute information), and attribute information regarding the state of a calibration curve (hereinafter, second attribute information). The first attribute information includes two types, i.e., "with On Hold" and blank (without On Hold), and the former has higher priority. The second attribute information includes three types, i.e., "without a calibration curve", "with a new calibration curve", and "with a validated calibration curve", and the priority is in this order.

With regard to the display priority, the first attribute information is superior to the second attribute information, and the priority of a reagent set "with On Hold" is highest. The reason for this is as follows: as for a reagent set "with On Hold", in order to recalculate an analysis parameter so as to immediately report it to the doctor or the patient, immediate creation of a calibration curve is required. In a case where there are a plurality of reagent sets whose first attribute information is the same, display ranking is determined in accordance with the priority of the second attribute information. It should be noted that, "with On Hold" is added only when no calibration curve has been created or when a calibration curve exists but the calibration curve has not been validated. Thus, the first attribute information being "with On Hold" can be combined with the second attribute information being "without a calibration curve" or "with a new calibration curve", but there exists no combination of attribute information being "with On Hold" and attribute information being "with a validated calibration curve".

"With On Hold" is added to the status information of a reagent set used in measurement of a sample without a validated calibration curve due to the automatic reagent switching function as described above. In S615 in FIG. 9, this attribute information is added to the status information of the reagent set. "Without a calibration curve" is set as default to the status information of a reagent set for which no calibration curve has been created and which has not been used in measurement of a sample. "With a new calibration curve" is added to the status information of a reagent set for which a calibration curve has been created but the calibration curve has not been validated by the operator. "With a validated calibration curve" is added to the status information of a reagent set having a validated calibration curve.

In the present embodiment, in a case where a sample has been measured by use of a reagent set for which no validated calibration curve has been created due to the automatic reagent switching function, the controller 20 adds, to the status information of the reagent set, attribute information ("with On Hold") for discriminating this reagent set from other reagent sets, and automatically extracts the reagent set to be a calibration curve creation target based on this attribute information, and displays the reagent set "with On Hold" in preference to other reagent sets. Accordingly, even in a case where a reagent set has been switched to a reagent set for which no calibration curve has been created due to the automatic reagent switching function, when a calibration curve is to be created after the measurement, work of searching for the reagent set used in the measurement of the on-hold sample can be saved, and thus, calibration curve creation can be quickly performed.

[S10: Calibrator Measurement/Calibration Curve Creation]

On the calibration curve order input screen 54, when a check box 58 has been checked, and the OK button has been pressed, the calibrator is measured by use of the reagent set designated in the designation region 55, and a calibration curve is created for the reagent set. Specifically, a rack R holding the calibrator is transported by the transport apparatus 3, and the transported calibrator is aspirated in the measurement apparatus 2. The measurement apparatus 2 measures the aspirated calibrator with respect to the designated measurement item, by use of the reagent set designated in the designation region 55. Obtained measurement data is inputted to the controller 20. Based on indicated values of the calibrator inputted in advance in the analyzer, the controller 20 creates a calibration curve from the relationship between the indicated values and measurement data. The created calibration curve is stored in the hard disk 404 in association with the information of the reagent set used in the creation of the calibration curve.

Figure 14:
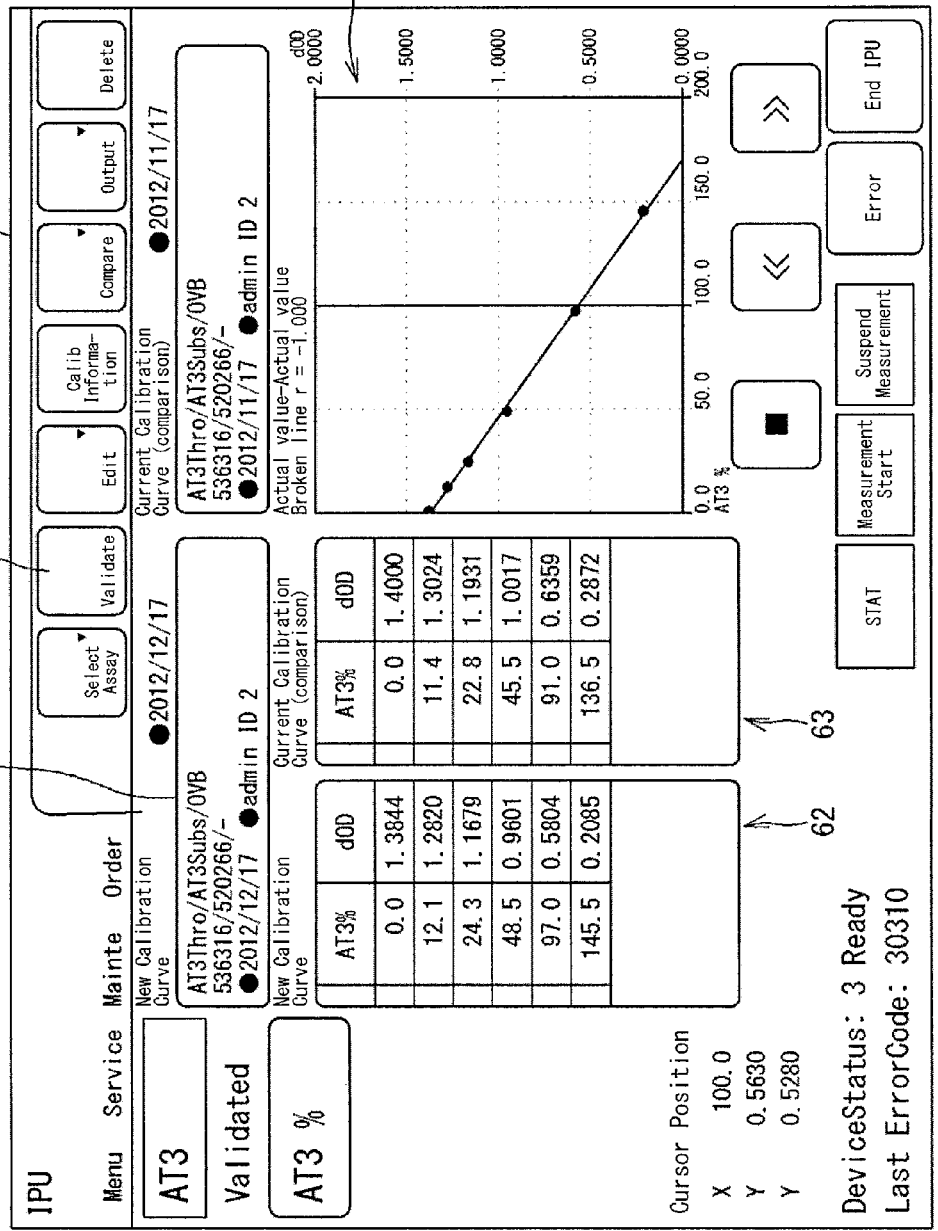
FIG. 14 shows one example of a calibration curve confirmation screen.

FIG. 14 shows a calibration curve confirmation screen 60 showing the created calibration curve. In a right portion of the calibration curve confirmation screen 60, a calibration curve display region 61 whose vertical axis is "dOD" and whose horizontal axis is "AT3%" is arranged. To the left thereof, a table 62 of a new calibration curve and a table 63 of a current calibration curve for comparison are arranged side by side. In a calibration curve information display region 65, the information of the reagent set used in creation of the calibration curve is displayed. By pressing a "validate" button 64 provided in an upper portion of the calibration curve confirmation screen 60, it is possible to validate the obtained calibration curve. When the calibration curve has been validated, the calibration curve stored in the hard disk 404 is provided with information indicating that the calibration curve has been validated, and in an upper left portion of the calibration curve confirmation screen 60, "Validated" is displayed.

[S11: Recalculation of On-Hold Sample]

Next, an analysis parameter is recalculated with regard to the on-hold sample. The operator returns the screen to the menu screen 100 and operates the job list icon 130, thereby causing the job list screen 46 to be displayed in the display part 21 again. When the record of the sample with "On Hold" displayed on the job list screen 46 is selected, and then, an operation menu of "data operation" in an upper portion of the screen is opened, a command of "manual calculation" appears. When the manual calculation command is selected, the controller 20 reads out, with regard to the selected sample, measurement data of the measurement item in the state of "On Hold", from the hard disk 404. By using, as a key, the lot information of the reagent set stored together with the read measurement data, the controller 20 specifies, from among calibration curves stored in the hard disk 404, a corresponding validated calibration curve and applies the read measurement data (dOD/min) to the validated calibration curve, to obtain a component concentration (AT3%) as the analysis parameter. The analysis parameter is stored into the hard disk 404. When these processes have been performed, as shown in FIG. 15, the display of the measurement state of the job list screen 46 changes from "On Hold" to "Complete" indicating that all measurement and analysis have been completed.

[Other Modifications]

It should be noted that the embodiment disclosed herein is merely illustrative in all aspects and should not be considered as being restrictive. The scope of the present invention is defined not by the description of the above embodiment but by the scope of the claims, and is intended to include meaning equivalent to the scope of the claims and all modifications within the scope.

The embodiment described above has illustrated a case where, when a reagent lot is changed due to automatic reagent switching, a calibration curve is created for a reagent set including a reagent of a new lot. However, a calibration curve may be created every time the combination of reagent vials is changed. For example, a unique ID may be assigned to each reagent vial, and a calibration curve may be created in association with the ID of each reagent vial relevant to the reagent set, instead of the information of reagent lots in the embodiment described above, whereby management may be performed.

Moreover, in the embodiment described above, in step S612 in FIG. 9, in a case where there is no validated calibration curve corresponding to the reagent set used in the sample measurement, information of "with On Hold" is added to the status information of the reagent set. However, the present invention is not limited thereto. For example, even in a case where there is a validated calibration curve corresponding to the reagent set used in the sample measurement, when a predetermined valid period has expired from the creation of the calibration curve, it may be determined that the calibration curve is not a valid calibration curve, and information of "with On Hold" may be added to the status information of the reagent set. Furthermore, in a case where the calibration curve is managed in association with IDs of reagent vials, when there is no calibration curve corresponding to the combination of the reagent vials used in the sample measurement, it may be determined as "without a calibration curve".

Further, in the embodiment described above, as a typical example where a reagent set without a calibration curve is to be used, a case has been described in which a reagent set is switched to a reagent set without a calibration curve in the middle of continuous measurement due to automatic reagent switching. However, the target to which the present invention is applied is not limited to a case of automatic reagent switching. It is understood that, for example, even a case where a reagent set without a calibration curve is used at the start of continuous measurement is included in the present invention.

In the embodiment described above, the reagent set with which on-hold measurement has been performed is displayed on the calibration curve order registration screen, and the operator presses the order button for calibration curve creation, whereby a calibration curve is created. However, the display of the reagent set may be omitted, and a calibrator may be measured by automatically using the reagent set "with On Hold", to create a calibration curve.

FIG. 16 is a flow chart showing operation performed by the sample analyzer 1 in a modification. After a calibrator has been set in the reagent storage 200 by the operator, the controller 20 determines whether calibration curve creation has been instructed (S101). When calibration curve creation has been instructed by the operator (Yes in S101), the controller 20 causes measurement of the calibrator to be performed by use of a reagent set having the highest priority from among stored reagent sets, to create a calibration curve (S102). Here, the priority that the controller 20 refers to is the same as the display priority of reagent sets described in the above embodiment. Thus, according to this flow chart, in a case where there is a reagent set "with On Hold", the reagent set "with On Hold" is automatically extracted without being designated by the operator, and a calibration curve can be automatically created.

In the embodiment described above, in a case where a sample has been measured by use of a reagent set for which no calibration curve has been created, the controller stores the reagent set and generates a calibration curve creation order for creating a calibration curve that uses the stored reagent set, and displays the order on the calibration curve order registration screen. However, the present invention can be applied also to quality control (QC) in the same manner.

For example, when a quality control sample has been measured, the controller 20 stores, into the hard disk 404, a quality control result together with the information of the reagent lot set used in the quality control. In a case where a sample has been measured by use of a reagent set for which quality control has not been performed due to automatic reagent switching, the controller 20 determines whether a quality control result corresponding to the reagent set used in the measurement of the sample is stored in the hard disk 404. When there is no corresponding quality control result, the controller 20 adds to the status information of the reagent set, information that the reagent set has been used in measurement without quality control performed, and stores the resultant status information in the hard disk 404. When displaying an order input screen for a quality control sample, the controller 20 may automatically extract the reagent set to which the status information indicating that the reagent set has been used in measurement without quality control performed has been added, and may automatically generate and display a quality control measurement order using the reagent set. In this case, upon receiving a quality control execution instruction from the operator, the controller may cause the measurement apparatus to execute quality control using the reagent set to which the status information has been added. Alternatively, displaying of the reagent set may be omitted, and upon issuance of instruction of quality control sample measurement, quality control sample measurement may be automatically executed by use of the reagent set to which the status information has been added.

What is claimed is:

1. A sample analyzer comprising:
   a measurement unit configured to measure a sample by use of a plurality of kinds of reagents in combination;
   a memory in which a calibration curve is stored in association with a reagent set; and
   a controller programmed to perform operations, comprising:
   performing automatic reagent switching, wherein after the automatic reagent switching, the reagent set comprises at least one of the plurality of kinds of reagents in a different reagent lot;
   determining, after measuring the sample by the measurement unit with the reagent set including at least one of the plurality of kinds of reagents in the different reagent lot, whether a calibration curve corresponding to the reagent set used in the measurement of the sample has been stored in the memory;
   when determining that the calibration curve corresponding to the reagent set used in the measurement of the sample has not been stored, controlling to store in the memory, information indicating that there is no calibration curve corresponding to the reagent set used in the measurement of the sample, and
   controlling to display, based on the information stored in the memory, the reagent set used in measurement of the sample and status information in association with the reagent set, the status information indicating that there is no calibration curve.

2. The sample analyzer of claim 1 wherein
the controller is programmed to control a display part to display a screen for inputting an order for generating a calibration curve, the screen displaying the reagent set used in measurement of the sample and the status information.

3. The sample analyzer of claim 2, wherein
the screen displays a plurality of reagent sets for each of which a calibration curve can be generated, and
the controller is further programmed to control the display part to display the reagent set associated with the status information indicating that there is no the calibration curve in preference to other reagent sets.

4. The sample analyzer of claim 2, wherein
the screen displays a list of a plurality of reagent sets for each of which a calibration curve can be generated, and
when displaying the list of the plurality of reagent sets, the controller is further programmed to control the display part to display a display rank of the reagent set associated with the status information indicating that there is no calibration curve higher than display ranks of other reagent sets.

5. The sample analyzer of claim 4, wherein
the screen includes:
a designation region in which a reagent set designated by an operator from among a plurality of reagent sets is displayed; and
an execution button for receiving an instruction to execute calibration curve creation,
when the execution button has been operated, the controller is programmed to execute calibration curve creation for the reagent set displayed in the designation region.

6. The sample analyzer of claim 5, wherein with regard to the sample measured by use of the reagent set for which no calibration curve has been stored, the controller is programmed to perform recalculating measurement data of the sample by use of a calibration curve generated after the measurement.

7. The sample analyzer of claim 1, wherein the controller is further programmed to:
receive an instruction to generate a calibration curve as to the reagent used in measurement of the sample and associated with the status information indicating that there is no calibration curve;
when having received the instruction, extract the reagent set for which no calibration curve has been stored and for which the information has been stored among possible combinations of reagent lots.

8. The sample analyzer of claim 7, wherein
the controller is further programmed to perform causing the reagent set used in measurement of the sample and associated with the status information indicating that there is no calibration curve, to be used in preference to other reagent sets in the measurement of the calibrator.

9. The sample analyzer of claim 1, wherein
in a case where, as reagents to be used for one measurement item, a reagent for which a calibration curve has been created and a reagent for which no calibration curve has been created are held in the reagent storage, the controller is programmed to control the measurement unit so as to use the reagent for which the calibration curve has been created in preference, and control the measurement unit so as to use the reagent for which no calibration curve has been created, in occurrence of shortage of the reagent for which the calibration curve has been created.

10. A sample analyzing method using a sample analyzer, the method comprising:
measuring a sample by use of a plurality of kinds of reagents in combination;
performing automatic reagent switching, wherein after the automatic reagent switching, a reagent set comprises at least one of the plurality of kinds of reagents in a different reagent lot;
determining, after measuring the sample with a reagent set whether a calibration curve corresponding to a reagent set used in measurement of the sample has been created, and
when determining that the calibration curve corresponding to the reagent set used in measurement of the sample has been not created, displaying the reagent set used in measurement of the sample and status information in association with the reagent set, the status information indicating that there is no calibration curve.

11. The sample analyzing method of claim 10, further comprising:
controlling to display the reagent set used in measurement of the sample and the status information on a screen for inputting an order to create the calibration curve.

12. The sample analyzing method of claim 11, wherein displaying the reagent set further comprises:
displaying the reagent set used in measurement of the sample and associated with the status information indicating that there is no calibration curve in preference to other reagent sets on the screen.

13. The sample analyzing method of claim 12, wherein displaying the reagent set further comprises displaying a display rank of the reagent set associated with the status information indicating that there is no calibration curve higher than display ranks of other reagent sets.

14. The sample analyzing method of claim 13, wherein the screen includes
a designation region in which a reagent set designated by an operator from among the plurality of reagent sets for each of which a calibration curve is creatable is displayed, and
an execution button for receiving an instruction to execute calibration curve creation, and
in the creating of a calibration curve, when the execution button has been operated, calibration curve creation is executed for the reagent set displayed in the designation region.

15. The sample analyzing method of claim 10, further comprising:
receiving an instruction to measure a calibrator;
creating a calibration curve based on the reagent set used in measurement of the sample and associated with the status information indicating that there is no calibration curve.

16. The sample analyzing method of claim 15, wherein
creating the calibration curve further comprises using the reagent set used in measurement of the sample and associated with the status information indicating that there is no calibration curve in preference to other reagent sets.

17. The sample analyzing method of claim 10, wherein
in a case where, as reagents to be used for one measurement item, a reagent for which a calibration curve has been created and a reagent for which no calibration curve has been created are held in the sample analyzer, the reagent for which the calibration curve has been created is used in preference to measure a sample, and the reagent for which no calibration curve has been created is used in occurrence of shortage of the reagent for which the calibration curve has been created.

18. A sample analyzer comprising:

a measurement unit configured to measure a sample by use of a plurality of kinds of reagents in combination; and a controller programmed to perform operations, comprising:

performing automatic reagent switching, wherein after the automatic reagent switching, a reagent set comprises at least one of the plurality of kinds of reagents in a different reagent lot;

determining, after measuring the sample by the measurement unit with the reagent set, whether a quality control result corresponding to the reagent set used in measurement of the sample has been stored in a memory;

when determining that the quality control result corresponding to the reagent set used in the measurement of the sample has not been stored, controlling to store, in the memory, information indicating that there is no quality control result corresponding to the reagent set used in the measurement of the sample, and controlling to display, based on the information stored in the memory, the reagent set used in measurement of the sample and status information in association with the reagent set, the status information indicating that there is no quality control result.

\* \* \* \* \*